United States Patent [19]

Le Goff et al.

[11] Patent Number: 5,386,057

[45] Date of Patent: Jan. 31, 1995

[54] PROCESS FOR THE PREPARATION OF ACYL ISOCYANATES

[75] Inventors: Philippe Le Goff, Villebon sur Yvette; Danièle Dewilde, Nandy, both of France; Noriyuki Tsuboniwa, Osaka; Satoshi Urano, Kyoto, both of Japan

[73] Assignees: Societe Nationale des Poudres et Explosifs, Paris, France; Nippon Paint Co. Ltd., Osaka, Japan

[21] Appl. No.: 100,177

[22] Filed: Aug. 2, 1993

[30] Foreign Application Priority Data

Aug. 18, 1992 [FR] France .............................. 92 10101

[51] Int. Cl.⁶ ...................................... C07C 249/00
[52] U.S. Cl. ................................. 562/871; 560/338; 560/340; 560/345; 560/347; 560/348; 560/336
[58] Field of Search ................ 562/871; 560/330, 336, 560/338, 340, 345, 347, 348

[56] References Cited

U.S. PATENT DOCUMENTS

| | | | |
|---|---|---|---|
| 3,155,700 | 11/1964 | Steyermark | 562/871 |
| 3,213,135 | 10/1965 | Speziale et al. | 562/871 |
| 3,450,747 | 6/1969 | Smith et al. | 562/871 |
| 3,664,990 | 5/1972 | Slagel | 562/871 |
| 3,850,985 | 11/1974 | Hagemann et al. | 562/871 |
| 4,344,962 | 8/1982 | Kühle et al. | 562/871 |
| 4,663,473 | 5/1987 | Geigel et al. | 562/871 |
| 4,769,485 | 9/1988 | Urano et al. | 562/871 |
| 4,925,982 | 5/1990 | Urano et al. | 562/871 |
| 4,970,319 | 11/1990 | Senet et al. | 562/871 |

FOREIGN PATENT DOCUMENTS

| | | | |
|---|---|---|---|
| 0143613 | 6/1985 | European Pat. Off. | 562/871 |
| 0202840 | 11/1986 | European Pat. Off. | 562/871 |
| 0756339 | 11/1970 | France | 562/871 |
| 2938110 | 4/1981 | Germany | 562/871 |
| 3010237 | 9/1981 | Germany | 562/871 |

OTHER PUBLICATIONS

J. Am. Chem. Soc. 62, 1595 (1940)–Dialkyl Biurets, Hill et al.
J. Org. Chem. 27, 3742 (1962) A One Step Synthesis of 1–Substituted Cyclopropanols.
J. Org. Chem. 28, 1805–1811, The Reaction of Oxalyl Chloride with Amides, Speziale et al (1961).
J. Org. Chem. Vo. 30, No. 12–Dec. 1965, The Reaction of Oxalyl Chloride with Amides, Speziale et al.
Heterocycles, vol. 94, 84147e, 1981, Sodium cefuroxime, Thompson.
Synthesis, Dec. 1988, p. 992–994, Convenient Preparation . . . Protected Amines.
J. Heterocycl. Chem. Nov.–Dec. 1990, A Convenient Synthesis of 1–aryl–3–methyl–1,2,4–triazolin–5–ones . . ., Ray et al, 2017.

*Primary Examiner*—Marianne M. Cintins
*Assistant Examiner*—Keith MacMillan
*Attorney, Agent, or Firm*—Cushman Darby & Cushman

[57] ABSTRACT

The invention concerns a process for the preparation of acyl isocyanates which consists of reacting oxalyl chloride with a salt selected from the group consisting of hydrohalides and sulphates of carboxamides and/or carbamates, unsubstituted on nitrogen, then heating the reaction mixture at a temperature between 30° and 150° C. The process is suitable for preparation of acyl isocyanates with excellent yields in easy to control operational conditions.

13 Claims, No Drawings

PROCESS FOR THE PREPARATION OF ACYL ISOCYANATES

The present invention concerns a new process for the preparation of acyl isocyanates. More specifically it concerns a process for the preparation of acyl isocyanates by means of oxalyl chloride.

Due to their excellent reactivity acyl isocyanates are very useful for forming ureas, carbamates and polymers.

The first process for the preparation of acyl isocyanates consisted of reacting acyl chloride with silver cyanate (J. Am. Chem. Soc., 62, 1595 (1940). Unfortunately this process cannot be used industrially due to the excessive cost of silver cyanate.

According to another process silver cyanate is replaced by isocyanic acid (U.S. Pat. No. 3,155,700). But this acid is very unstable and very difficult to prepare by decomposition of isocyanuric acid at a very high temperature such as 620° C.

Between 1962 and 1965, A. J. Speziale et al. developed a process for the preparation of acyl isocyanates by reacting amides with oxalyl chloride (J. Org. Chem., 27, 3742 (1962), 28, 1805 (1963), 30, 4306 (1965). Unfortunately this process gives very variable results depending upon the starting amide used, and the yield of acyl isocyanates particularly from aliphatic amides is very weak. Furthermore the reaction is generally very strongly exothermic and makes it very difficult to obtain thermosensitive isocyanates. It is very difficult to control heat release. The capacity of the heat exchangers used to cool down the reaction medium can very rapidly become insufficient and a dangerous runaway reaction can sometimes occur.

S. Urano et al. recently improved this process in the production of acryloyl and methacryloyl isocyanates (U.S. Pat. No. 4,925,982). If these isocyanates can be produced with an acceptable yield, they are unfortunately not pure. In fact the corresponding β-halopropionyl isocyanates are formed at the same time. It is therefore necessary to separate the two types of isocyanate.

S. Urano et al. then suggested preparing alkenoyl isocyanates by decomposition of a oxazolinedione hydrohalide formed by gradually adding amide to the oxalyl chloride solution (U.S. Pat. No. 4,769,485). However this formation is also very strongly exothermic and difficult to control. The process can also be dangerous because all the oxalyl chloride required is present in the reactor at the same time. The oxalyl chloride therefore has to be diluted in a large quantity of solvent. Problems then arise with solubility and agitation. The productivity of the process is thus very weak.

The purpose of the present invention is to offer a process for the preparation of acyl isocyanates which does not have the disadvantages of previous processes and which enables many acyl isocyanates of a high purity to be obtained without danger and with high yields.

According to the present invention the process for the preparation of acyl isocyanates consists of reacting oxalyl chloride with a salt selected from the group consisting of hydrohalides and sulphates of carboxamides and/or carbamates, unsubstituted on nitrogen, and their mixtures, and then heating the reaction mixture at a temperature between 30° and 150° C.

Carboxamide and/or carbamate salts used as the starting substances in the present invention are available commercially or can be prepared easily particularly by reacting amides and carbamates with sulphuric acid or halohydric acids such as hydrochloric, hydrobromic or hydroiodic acid.

All carboxamides and carbamates unsubstituted on nitrogen which can form a salt with the above-mentioned acids can be reacted with oxalyl chloride.

For economic reasons, it is preferable to use amide hydrochlorides and carbamate hydrochlorides. These hydrochlorides can be prepared for example by passing a stream of gaseous hydrochloric acid, preferably anhydrous, into a suspension or solution of carboxamide or carbamate in an inert organic solvent medium. A minimum equivalent of hydrochloric acid per equivalent of amide or carbamate function to be salified must be used. The salt can be prepared in a solvent medium which can be used for the reaction with oxalyl chloride thus avoiding the need to separate the salt and the solvent and then to introduce a new solvent. In this case, one must ensure that the carboxamide or carbamate has been completely transformed into salt before reacting it with the oxalyl chloride.

The process according to the invention is particularly suitable for the transformation of salts of the formula:

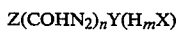

$$Z(COHN_2)_n Y(H_m X)$$

wherein Z represents a mono or divalent radical,
- aliphatic with 1 to 20 carbon atoms, linear or branched, saturated or unsaturated, substituted or unsubstituted,
- cycloaliphatic with 5 to 7 carbon atoms, saturated or unsaturated, substituted or unsubstituted,
- araliphatic with 7 to 20 carbon atoms, linear or branched, saturated or unsaturated, substituted or unsubstituted,
- phenyl, phenylene, naphthyl or naphthylene, substituted or unsubstituted,
- heterocyclic with 5 or 6 members including one or several heteroatoms from amongst oxygen, nitrogen or sulphur, saturated or unsaturated, substituted or unsubstituted, or Z represents a group —R—O—, —O—R—O or —R—O in which R represents a mono- or divalent radical,
- aliphatic with 1 to 8 carbon atoms, linear or branched, saturated or unsaturated, substituted or unsubstituted,
- cycloaliphatic with 5 to 7 carbon atoms, saturated or unsaturated, substituted or unsubstituted,
- araliphatic with 7 to 11 carbon atoms, linear or branched. saturated or unsaturated, substituted or unsubstituted,
- phenyl, phenylene, naphthyl or naphthylene, substituted or unsubstituted, n represents the number 1 or 2,
m represents the number 1 or 2,
y represents the value n/m
X represents a halogen atom, the group $SO_4$ or $HSO_4$.

The substituent(s) of Z may in particular be chosen from the group consisting of halogen atoms and hydrocarbyloxy and halohydrocarbyloxy radicals with 1 to 20 carbon atoms, for example such as methoxy, phenyloxy and chlorophenyloxy.

Where Z represents a group including one or more aromatic or heteoaromatic radicals, the substituent(s) of these radicals can also be chosen from amongst hydrocarbyl and halohydrocarbyl radicals with 1 to 20 carbon atoms, for example methyl, ethyl, trifluoromethyl, phenyl, chlorophenyl, fluorophenyl, and the nitro group.

Unsaturated links of aliphatic or araliphatic radicals can be of the ethylenic or acetylenic type. In cycloaliphatic or nonaromatic heterocyclic radicals they are of the ethylenic type.

Halogen atoms should preferably be chosen from amongst chlorine, bromine and fluorine atoms.

Heteroatoms of heterocyclic radicals should preferably be chosen from amongst oxygen and nitrogen atoms.

X can represent a halogen atom, such as chlorine, bromine and iodine. For economic reasons, X should preferably be a chlorine atom.

The reaction can be shown by the following general formula:

$$Z(CONH_2)_n Y(H_mX) + nClCOCOCl \rightarrow Z(CON-CO)_n + 2nHCl + nCO + yH_mX$$

Among the acyl isocyanates which can usefully be prepared by the process according to the invention are the following:
  acetyl isocyanate (Z=methyl), propionyl isocyanate (Z=ethyl), butyrylisocyanate (Z=propyl), isobutyryl isocyanate (Z=isopropyl), pivaloyl isocyanate (Z=t-butyl), stearoyl isocyanate (Z=CH$_3$(CH$_2$)$_{16}$—), trichloroacetyl isocyanate (Z=—CCl$_3$);
  cyclopentanecarbonyl isocyanate (Z=cyclopentyl), cyclohexanecarbonyl isocyanate (Z=cyclohexyl); phenylacetyl isocyanate (Z=benzyl);
  acryloyl isocyanate (Z=vinyl), methacryloyl isocyanate (Z=isopropenyl), cinnamoyl isocyanate (Z=C$_6$H$_5$—CH=CH—),
  benzoyl isocyanate (Z=phenyl), p-methoxybenzoyl isocyanate (Z=p-methoxyphenyl), 2,6-difluorobenzoyl isocyanate (Z=2,6-difluorophenyl), 2,6-dichloro-3-nitrobenzoyl isocyanate (Z=2,6-dichloro-3-nitrophenyl), and 1- or 2-naphthoyl isocyanate (Z=naphthyl), 5-chloro-2-nitrobenzoyl isocyanate (Z=5-chloro-2-nitrophenyl), 5-nitrofuroyl isocyanate (Z=5-nitrofuryl);
  succinyl isocyanate (Z=—CH$_2$CH$_2$—, n=2), adipoyl isocyanate (Z=—(CH$_2$)$_4$—, n=2), terephthaloyl isocyanate (Z=p —C$_6$H$_4$—, n=2); fumaryl isocyanate (Z=—CH=CH—, n=2),
  methoxycarbonyl isocyanate (Z=CH$_3$O—), ethoxycarbonyl isocyanate (Z=C$_2$H$_5$O—), t-butoxycarbonyl isocyanate (Z=t-butyl-O-), 2,2,2-trichloroethoxycarbonyl isocyanate (Z=Cl$_3$CCH$_2$O—), benzyloxycarbonyl isocyanate (Z=C$_6$H$_5$—CH$_2$O—), phenoxycarbonyl isocyanate (Z=C$_6$H$_5$—O—),
  bis 1,4-(oxycarbonyl) butylene di-isocyanate.

The process according to the invention can be undertaken without solvent, but it is preferable to use a solvent or mixture of organic solvents that are aprotic and inert as regards the components, and preferably anhydrous. Suitable solvents include halogenated or unhalogenated aliphatic hydrocarbons such as hexane, dichloromethane, and 1,2- dichloroethane; cycloalkanes such as cyclohexane and methylcyclohexane; and aromatic hydrocarbons such as toluene, xylenes, chlorobenzene and o-dichlorobenzene. For preparing alkenoyl isocyanates, in particular methacryloyl isocyanate, a mixture of o-dichlorobenzene and a light alkane such as n-hexane, n-heptane or cyclohexane is totally suitable.

The oxalyl chloride is preferably added to the medium containing the carboxamide or carbamate salt, and particularly on a gradual basis so that it is consumed as it is added, thus limiting the risks involved. As it is in liquid form, it is all the easier to add.

An approximately stoichiometric quantity of oxalyl chloride is required per function of amide salt or carbamate salt to be transformed: preferably a 1 to 1.2 equivalent of oxalyl chloride is added per function of amide or carbamate salt, i.e. an excess quantity of between 0 and 20%.

Unlike earlier processes in which the reaction of oxalyl chloride with an amide is accompanied by considerable heat release in the reaction medium, the reaction of oxalyl chloride with the amide or carbamate salt according to the process used in the invention is a globally athermic reaction requiring no heat transfer and in particular no cooling. The reaction may thus be carried out at ambient temperature, generally at or between 15° C. and 30° C. when the compounds are stable at this temperature under the reaction conditions, and there is no risk of a runaway reaction.

Once the oxalyl chloride has been added, the reaction mixture is left agitating if necessary, so that all the salt reacts. The reaction mixture is then heated to a temperature between 30° and 150° C., preferably between 35° C. and 130° C.

The solvent medium is generally selected as having a boiling point high enough for such temperatures to be reached. Should the solvent boiling point be too low, the solvent medium may be changed before heating or a suitable solvent may be added.

The acyl isocyanate thus obtained is separated out from the reaction mixture by standard techniques, e.g. filtration or distillation either at atmospheric pressure or under partial vacuum.

It is possible to increase the yield of certain isocyanates, e.g. methacryloyl isocyanate, by waiting for the precipitation of the intermediate compound generally formed during the reaction, before heating the reaction mixture. Should precipitation not occur spontaneously, it may be initiated by any accepted method, for example by adding to the reaction mixture a small quantity of the intermediate compound obtained from an earlier operation and/or by gentle heating to temperatures up to 30° C.

The process described in the present invention may also be carried out in two distinct stages. In this case, the oxalyl chloride and carboxamide or carbamate salt reaction is carried out as described above and the product(s) separated out from the reaction mixture by standard techniques. The product(s) may then be kept as long as required before being transformed by heating as described above.

The process described in the invention is suitable for industrial preparation at economic levels and with no risk of many isocyanates derived from carboxamides and carbamates. In particular, this new process allows excellent yields of acyl isocyanates derived from aliphatic amides, which previously were obtainable only with poor yields from the A. J. Speziale process et al.

Acyl isocyanates are extremely useful in the preparation of a number of products in the fields of pharmaceuticals, agrochemicals and polymers. One example is acetyl isocyanate, used as a key intermediate in the preparation of triazolinones (J. Heterocyl. Chem 1990, 27/(7), 2017). Trichloroacetyl isocyanate is widely used to form carbamate functions during the synthesis of antibiotics, in particular "céfuroxime" (CA 94 84147 e). Other antibiotics are produced using t-butoxycarbonyl, 2,2,2-trichloroethoxycarbonyl and benzyloxycarbonyl isocyanates.

Copolymerization of the highly reactive methacryloyl isocyanate produces materials suitable for cross-linkable coatings, used in dental adhesives or acrylic elastomers. New drugs such as lipoxygenase inhibitors are made from benzoyl isocyanate. Substituted benzoyl isocyanates such as 2,6-difluorobenzoyl isocyanate are widely used in the production of many benzoyl ureas insecticides. Protected amines may be synthesized directly from benzoyloxycarbonyl isocyanate. (Synthesis, Dec. 1988, p. 992).

The following examples are designed to illustrate the present invention without limiting it.

All the reactions are carried out in an inert atmosphere using readily available raw materials.

The hydrochloric acid used is anhydrous.

EXAMPLE 1

Preparation of Benzoyl Isocyanate

Quantities of 36.3 g (0.3 mol) of benzamide and 200 g of dichloromethane are charged into a 250 ml reactor. While stirring the mediums, a quantity of 13.8 g (0.378 mol) of gaseous hydrochloric acid is added in over 44 minutes, bubble by bubble. As the HCl is added, the temperature rises from 21.3° C. to 38° C.

The benzamide hydrochloride precipitates as a white solid. The $^1$H NMR spectrum confirms that the benzamide has disappeared and its hydrochloride obtained: (CDCl$_3$, ppm):
  7.53 (2H arom., t)
  7.68 (1H arom., t)
  8.10 (2H arom., t)
  11.0–8.5 (H of NH)

A quantity of 42 g (0.33 mol) of oxalyl chloride is then added one drop at a time to the hydrochloride suspension, while agitation continues, over a period of 39 minutes without cooling.

The temperature of the medium falls gradually from 21.3° C. to 16° C. and HCl is given off vigorously.

Agitation is continued for a further 30 minutes, then reflux-heated (temperature of medium: 38° to 46° C.; temperature of oil bath: 60° C.) until the suspended solid disappears.

Heating is discontinued after 3 hours and the medium allowed to cool.

The rate of transformation of the benzamide into benzoyl isocyanate as determined by 1H NMR is 94% (CDCl$_3$; ppm):
  aromatic protons at 7.33–7.47;
  7.51–7.64 and
  7.91–8.02.

EXAMPLE 2

Preparation of Benzoyl Isocyanate from Benzamide (Comparative Example)

This example does not form part of the invention and is given solely to demonstrate the advantages offered by the process described in the invention.

The apparatus is the same as that used in Example 1.

Over a period of 38 minutes, 42 g (0.33 mol) of oxalyl chloride are added drop by drop to an agitated solution-suspension of 36.3 g (0.3 mol) of benzamide in 200 g of dichloromethane. The temperature rises from 19.6° C. to 30.5° C. as soon as one-third of the oxalyl chloride is added.

Once all the oxalyl chloride has been added, the same procedure as in Example 1 is followed. In this case however, it is seen that the white solid formed does not completely disappear.

The degree of transformation into benzoyl isocyanate measured in the same way as before is 88.6%.

EXAMPLE 3

Preparation of Methacryloyl Isocyanate

Quantities of 102 g (1.2 mol) of methacrylamide, 240 g of ortho-dichlorobenzene, and 50 g of hexane are put in a 1000 ml reactor.

The suspension is agitated at ambient temperature, and gaseous hydrochloric acid is introduced without cooling the medium. After introduction of 1.2 to 1.3 eq. (equivalent) of HCl with respect to the methacrylamide, the medium is cooled to 18° C. The hydrochloride obtained from the methacrylamide is characterized by its $^1$H NMR spectrum:
(CDCl$_3$; ppm):
  2.15 (CH)$_3$
  6.0 (H, ethylenic)
  6.5 (H, ethylenic)

Over a period of 45 minutes, 167 g (1.1 eq.) of oxalyl chloride are added drop by drop while the suspension is agitated. Absolutely no heat is released.

The product formed is precipitated, if necessary by adding a small quantity of the same product obtained in a previous operation, and/or by heating slightly to 30° C.

When precipitation are complete, 310 g of hexane is added over a period of one hour.

The reactor medium is then heated at 72°–74° C. until there is a change in appearance accompanied by a rise in temperature (+5° C. approx.) (takes about 2 hours).

Heating is continued for a further 20 minutes, and the medium is then cooled to ambient temperature.

The degree of transformation of methacrylamide into methacryloyl isocyanate as determined by its $^1$H NMR spectrum is 90–100%.

EXAMPLE 4

Preparation of Trimethyl Acetyl Isocyanate 30 g (0.29 mol) of trimethylacetamide and 200 g of orthodichlorobenzene are put in a 500 ml reactor. Over a period of 35 minutes, 14 g (0.38 moll of gaseous hydrochloric acid are bubbled into the agitated medium. During this phase the temperature rises from 20.0° C. to 31.5° C. The suspended solid, i.e. the trimethylacetamide (which is not completely soluble in the medium) disappears. This produces a clear trimethylacetamide hydrochloride, as determined by the $^1$H NMR spectrum.

41 g (0.32 mol) of oxalyl chloride are then added drop by drop to the above solution at 19.6° C. While it is added (over a period of 35 minutes), the temperature hardly changes, remaining between 19° and 21° C.

The solution is agitated for 10 minutes at 30° C., then heated for one hour in a 80° C. oil bath, the temperature of the medium rising from 65° to 80° C. The formation of the expected product is followed by infrared spectrometry (NCO band at 2,220 cm$^{-1}$).

The trimethylacetyl isocyanate is then isolated by distilling at reduced pressure (boiling point bp: 62° C./110 mm Hg)

Yield: 75%

¹N MNR (CDCl₃): 1.15 ppm (s, t-butyl).

EXAMPLE 5

Preparation of Methoxycarbonyl Isocyanate
CH₃—O—CO—NCO

A quantity of 40 g (0.53 mol) of methyl carbamate and 200 g of ortho-dichlorobenzene is put in a 500 ml reactor. As described in Example 4, 28 g (0.75 mol) of gaseous hydrochloric acid are bubbled in 90 minutes. The temperature rises from 20° C. to 29° C. This produces carbamate hydrochloride in the form of an emulsion in the solvent, as determined by the ¹H MNR spectrum (CDCl₃): —NH₂ proton group at 5.04 ppm.

A quantity of 74.5 g (0.59 mol) of oxalyl chloride is then added to the above emulsion drop by drop for 50 minutes. During this time the temperature rises from 20° C. to 22° C.

The emulsion is agitated for a further 30 minutes at 26° C., then the medium is heated from 70° to 130° C. for 4 hours and 30 minutes.

The methoxycarbonyl isocyanate is then isolated by distillation under atmospheric pressure (bp: 68°–70° C.)

Yield: 55%

¹H MNR (CDCl₃): 3.82 ppm (s, methyl).

EXAMPLE 6

Preparation of Phenylacetyl Isocyanate
C₆H₅—CH₂—CO—NCO

Quantities of 20 g (0.148 mol) of phenylacetamide and 150 g of 1,2-dichloroethane are put in a 250 ml reactor. As described in Example 4, 12 g (0.32 mol) of gaseous hydrochloric acid are bubbled in in 60 minutes. The temperature rises from 21.5° C. to 42.2° C. A white, solid suspension of hydrochloride is thus produced: its structure is confirmed by ¹H NMR (CDCl₃):

CH₂ protons: 3.75 ppm
NH₂ protons: 3.8–3.9 (large)

While the above suspension is agitated, 22 g (0.173 mol) of oxalyl chloride are added drop by drop for 35 minutes. During this operation the temperature of the medium remains close to 19° C. and the color of the suspended solids changes from white to yellow.

The solution is agitated for a further 30 minutes at 30° C. The intermediate product is filtered out and put in suspension in 150 g of agitated ortho-dichlorobenzene. The suspension is brought to a temperature between 136° and 146° C. for 8 hours.

The solvent is then evaporated off under vacuum and the phenylacetyl isocyanate is purified by distillation at reduced pressure (bp: 78° C./3–5 mm Hg).

Yield: 47%

¹H NMR (CDCl₃): aromatic protons: 7.37–7.04 ppm (m) CH₂ protons: 3.66 ppm

EXAMPLE 7

Preparation of Phenylacetyl Isocyanate from Phenylacetamide (Comparative Example)

This example is not part of the invention.

Quantities of 20 g (0.148 mol) of phenylacetamide and 150 g of 1,2-dichloroethane are put in a 250 ml reactor. 22 g (0.173 mol) of oxalyl chloride are then added to the agitated suspension in 35 minutes. The temperature rises from 22° C. to 33.7° C.

The procedure then follows the steps of Example 6 from the separation of the intermediate product.

After distillation at reduced pressure under the same conditions as above, phenylacetyl isocyanate is produced with yield of only 28%.

EXAMPLE 8

Preparation of Phenoxycarbonyl Isocyanate
C₆H₅—O—CO—NCO 41.14 g (0.3 mol) of phenyl carbamate and 200 g of 1,2-dichloroethane are put in a 300 ml reactor. 15.3 g (0.42 mol) of gaseous hydrochloric acid are then bubbled into the suspension-solution for 100 minutes. The temperature rises from 22° C. to 26° C. Solid white phenylcarbamate hydrochloride precipitates out.

The ¹H NMR spectrum confirms this form. (CDCl₃, ppm):

7.12–7.15 (2H arom.,)
7.15–7.22 (1H atom.,)
7.35–7.39 (2H atom.,)
5.16 (H of NH)

Over a period of 40 minutes, and without cooling, 41.91 g (0.33 mol) of oxalyl chloride are added drop by drop to the phenylcarbamate hydrochloride suspension obtained.

The reaction temperature is between 20° C. and 22° C. The reactor is agitated for a further 30 minutes at 22° C.

The reaction mixture is then heated from 45° C. to 93° C. for 7 hours.

The solvent is then evaporated off under reduced pressure and the phenoxycarbonyl isocyanate is purified by distillation under reduced pressure (bp: 125° C./5 mm Hg).

Yield: 57.6%

¹H NMR (CDCl₃): 7.26–7.35 ppm (phenyl)

EXAMPLE 9

Preparation of 5-chloro-2-nitrobenzoyl isocyanate

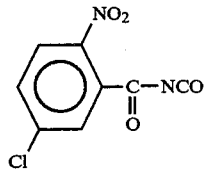

Quantities of 39.965 g (0.199 mol) of 5-chloro-2-nitrobenzamide and 200 g of 1,2-dichloroethane are put in a 500 ml reactor. A quantity of 11.0 g (0.31 mol) of gaseous hydrochloric acid is bubbled into the suspension-solution for 80 minutes. The temperature rises from 25° C. to 35° C.

Solid white 5-chloro-2-nitrobenzamide hydrochloride precipitates out.

Its structure is confirmed by its ¹H NMR spectrum: (DMSO, ppm):

7.708–7.738 (H arom.,)
7.787–7.811 (H arom.,)
7.924–8.104 (H arom.,)
8.207 (H of NH)

Over a period of 40 minutes, and without cooling, 27.94 g (0.22 mol) of oxalyl chloride are added drop by drop to the hydrochloride suspension. The reaction temperature rises from 18° C. to 26° C. The reactor is then agitated for a further 30 minutes at 25° C., then heated at 65° C. for an hour and a half.

In order to characterize the isocyanate formed, it is reacted with aniline, forming 23.8 g of N-(5-chloro-2-nitrobenzoyl)-N' phenylurea.

The yield calculated from the quantity of this product obtained is 38.4%.

EXAMPLE 10

Preparation of 2,6-difluorobenzoyl Isocyanate

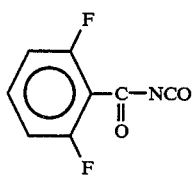

Over a period of 55 minutes, 11.8 g ( 0.32 mol ) of gaseous hydrochloric acid are introduced into a suspension-solution of 39.25 g ( 0.25 mol ) of 2,6-difluorobenzamide in 300 g of dichloromethane. The temperature of the reaction medium rises from 21° C. to 25° C. The formation of hydrochloride is checked by $^1$H NMR analysis. The signal for one of the $NH_2$ protons of the salt is displaced slightly (6.38 ppm) relative to the signal for the same $NH_2$ proton of the amide (6.33 ppm). The signal of the HCl proton is 1.79 ppm (large s)

The 2,6-difluorobenzamide hydrochloride solution-suspension are left standing for 20 minutes, then 35 g (0.276 mol) of 23° C. oxalyl chloride is added in 50 minutes. The temperature drops from 23° C. to 19.6° C. and HCl is seen to be released.

The reaction medium is left standing for an hour and half, and is then heated at 40° C. for three and a half hours. 38 g of 2,6-difluorobenzoyl isocyanate are then isolated by distillation at reduced pressure:
(bp: 103°–106° C./3 mm Hg)
Yield: 83%
IR: 2,250 cm$^{-1}$ (NCO)

EXAMPLE 11

Preparation of cinnamoyl isocyanate

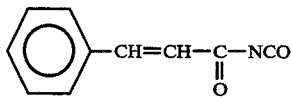

Over a period of 30 minutes, 10.3 g (0.28 mol) of gaseous hydrochloric acid are let into a suspension-solution of 25 g (0.17 mol) of cinnamide in 150 g of 1,2-dichloroethane. Since the temperature rises from 21° C. to 38° C., the medium is cooled. The formation of cinnamide hydrochloride is checked by $^1$H NMR analysis:
(CDCl$_3$, ppm):
2.045 (large s, HCl)
5.65–6.1 (large, 2H, NH$_2$)
6.48 (d, 1H, vinyl J=15.7 Hz)
7.36–7.44 and 7.48–7.58 (m, 5H, arom.)
7.67 (d,1H, vinyl J=15.7 Hz)

The reaction mixture is left standing for 50 minutes at ambient temperature, then 24 g (0.189 mol) of oxalyl chloride at 23° C. are added in 30 minutes. The temperature goes from 23° C. to 22° C. The reaction mixture is then heated at 80°–85° C. for 1.6 hours, then cooled.

The medium is distilled at reduced pressure and 13.7 g of cinnamoyl isocyanate are obtained.
(bp: 159°–167° C./3 mm Hg)
Yield: 46.6%
IR: 2,250 cm$^{-1}$ (NCO)

EXAMPLE 12

Preparation of Cyclohexanoyl Isocyanate

Over a period of 50 minutes, 10.2 g (0.28 mol) of gaseous hydrochloric acid are introduced into a suspension-solution of 25.4 g (0.20 mol) of carboxamide cyclohexane in 100 g of 1,2dichloroethane. The temperature of the reaction mixture rises from 23° C. to 45° C., producing a clear solution. The formation of hydrochloride is checked by $^1$H NMR analysis:
(CDCl$_3$, ppm):
1.20–2.06 (m, 10H, CH$_2$)
2.67–2.82(m, 1H, CH)
9.0–9.4 (large, 1H, NH$_2$)
9.65–10.1 (large, 1H, NH$_2$)
11.5–11.9 (large s, 1H, HCl)

27.9 g (0.22 mol) of oxalyl chloride at 28° C. are then added in 40 minutes. The temperature drops from 28° C. to 18° C. The reaction medium is then heated at 85°–91° C. for four hours, then cooled.

10.71 g of cyclohexanoyl isocyanate are isolated by distillation at reduced pressure:
(bp: 88°–90° C./3 mm Hg)
Yield: 35%
IR: 2,238 cm$^{-1}$ (NCO)

EXAMPLE 13

Preparation of p-methoxybenzoyl Isocyanate

Over a period of 25 minutes, 10.1 g (0.28 mol) of gaseous hydrochloric acid are let into a suspension-solution of 30.2 g (0.2 mol) of p-methoxybenzamide in 200 g of dichloromethane. The temperature of the reaction mixture rises from 17° C. to 31° C. The formation of hydrochloride is checked by $^1$H NMR analysis:
(CDCl$_3$, ppm):
3.78 ppm (s, 3H, CH$_3$O)
4.2–4.8 ppm (large, 1H, NH$_2$HCl)
6.98–7.88 (each d, 2H, atom. J: 8.65 Hz)

The reaction mixture is left standing for 55 minutes at ambient temperature, then 27.9 g (0.22 mol) of oxalyl chloride at 22.6° C. are added over a 50-minute period. The temperature of the medium drops from 24° C. to 19° C. The reaction medium is then heated at 39°–43° C. for 3 hours and then cooled.

A quantity of 31.5 g of p-methoxybenzoyl isocyanate is isolated by distillation at reduced pressure.
(bp: 113°–116° C./2 mm Hg)
Yield: 89%
IR: 2,245 cm$^{-1}$ (NCO)

EXAMPLE 14

Preparation of Stearoyl Isocyanate

Over a period of 2.9 hours, 14.1 g (0.38 mol) of gaseous hydrochloric acid are let into a suspension-solution of 28.3 g (0.1 mol) of stearylamide in 200 g of dichloromethane. Since the medium gradually solidifies, a further 100 g of dichloromethane are added. The temperature rises from 17° C. to 21.7° C. The formation of the salt is checked by $^1$H NMR analysis:
(CDCl$_3$, ppm):
0.88 (t, 3H, CH$_3$, J=6.8 Hz)

1.22–1.3 (large m, 30H, CH$_2$)
1.64 (large, 1H, NH$_2$)
2.09 (large, 1H, NH$_2$)
2.24 (m, 2H, CH$_2$CO)
5.6 (large, 1H, HCl)

A quantity of 13.9 g (0.11 mol) of oxalyl chloride at 20.7° C. is then added to the reaction medium over a 30-minute period. The temperature of the medium drops from 20.6° C. to 19° C.

The reaction mixture is then heated at 39°–40° C. for 4 hours and no isocyanate is seen to form. In order to heat to a higher temperature, the solvent is changed, the dichloromethane being replaced by 1,2-dichloroethane by azeotropic distillation.

The reaction mixture is then heated to 84°–86° C. for six hours, then allowed to cool.

A quantity of 12.2 g of stearoyl isocyanate is isolated by distillation at reduced pressure:
(bp: 79°–82° C./4 mm Hg)
Yield: 39%
IR: 2245 cm$^{-1}$ (NCO)

EXAMPLE 15

Preparation of Phenylacetyl Isocyanate

A suspension of 12 g (0.07 mol) of phenylacetamide hydrochloride is formed with 80 g of o-dichlorobenzene.

While agitating this suspension, a quantity of 10 g (0.079 mol) of oxalyl chloride is added over a 30-minute period. Agitation continues for a further 30 minutes, at 30° C., then the suspension is heated at between 136° and 146° C. over a further eight hours.

The solvent is evaporated off under reduced pressure, and a quantity of 5.64 g of phenylacetyl isocyanate is obtained by distillation at reduced pressure.
(bp: 78° C./3–5 mm Hg)
Yield: 50%

EXAMPLE 16

Preparation of 2-methylpropanoyl Isocyanate

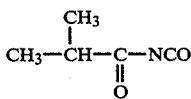

Over a period of 1.9 hours, a quantity of 11.4 g (0.31 mol) of gaseous hydrochloric acid is let into a suspension-solution of 17.4 g (0.2 mol) of 2-methylpropionamide in 200 g of 1-2-dichloroethane. The temperature of the reaction medium rises from 20.4° C. to 41.9° C. The formation of hydrochloride is checked by $^1$H NMR analysis:
(CDCl$_3$, ppm):
 1.35 (d, 6H, CH$_3$)
 2.9–3.1 (m, 1H, CH)
 9.6–10.3 (large, NH$_2$HCl).

The reaction medium is left standing for 30 minutes, then 27.9 g (0.22 mol) of oxalyl chloride, at 20.7° C. are added over a 30 minutes period. The temperature of the medium drops from 25.1° to 18° C. The reaction medium is then heated at 83°–86° C. for 3.2 hours and then cooled.

The 2-methylpropanoyl isocyanate obtained is characterized by $^1$H NMR and IR analysis:
(CDCl$_3$, ppm):
 1.14 (d, 3H, CH$_3$)
 1.77 (d, 3H, CH$_3$)
 2.32–2.68 (m, 1H, CH)
IR: 2245 cm$^{-1}$ (NCO).

A quantity of 18.4 g (0.4 mol) of ethanol is then added to the reaction medium to transform the isocyanate into carbamate. The yield calculated from the quantity of the carbamate obtained is 57.6%.

EXAMPLE 17

Preparation of 1-naphthyloyl Isocyanate

Quantities of 4.496 g (0.026 mol) of 1-naphthylamide and 50 g of toluene are introduced into a 100 ml reactor. 6.1 g (0.17 mol) of gaseous hydrochloric acid are then bubbled into the stirred suspension-solution of 1-naphthylamide over a 45 minute period. During this addition, the temperature of the medium rises from 24° C. to 31° C. A white, solid suspension of 1-naphthylamide hydrochloride is thus produced. It is characterized by its $^1$H NMR spectrum:
(DMSO, ppm): 7.2 (H, naphtalenic).

A quantity of 3.69 g (0.031 mol) of oxalyl chloride is then added drop by drop to the stirred 1-naphthylamide hydrochloride suspension, over a 40 minute period, without cooling. The temperature of the medium decreases from 27° C. to 24° C. The reaction medium is stirred for a further 30 minutes at 24° C., and it is then heated between 75° C. and 95° C. for 3.5 hours.

The remaining solids are removed by filtration under reduced pressure. The IR spectrum of the naphthyloyl isocyanate obtained shows an absorption at 2240 cm$^{-1}$.

The yield calculated from the quantity of the urea produced by reaction of the naphthyloyl isocyanate with aniline is 98%.

EXAMPLE 18

Preparation of Succinyl Isocyanate 15.1 g (0.31 mol) of succinamide and 300 g of 1,2-dichloroethane are introduced into a 500 ml reactor. 14.6 g (0.41 mol) of gaseous hydrochloric acid are then bubbled into the stirred suspension-solution of succinamide for 20 minutes. During this addition, the temperature of the medium rises from 24° C. to 28° C. A white, solid suspension of succinamide hydrochloride is thus produced. It is characterized by its $^1$H NMR spectrum:
(DMSO, ppm): 2.24 (H, methylenic).

66.3 g (0.52 mol) of oxalyl chloride are then added drop by drop to the stirred succinamide hydrochloride suspension, for 60 minutes, without cooling. The temperature of the medium decreases from 26° C. to 25° C. The medium is stirred for a further 60 minutes at 25° C., and it is then heated at 81° C. for 9 hours.

The remaining solids are then removed by filtration under reduced pressure. The IR spectrum of the succinyl isocyanate obtained shows an absorption at 2240 cm$^{-1}$. The yield calculated from the urea produced by reaction of the succinyl isocyanate with aniline is 77.3%.

EXAMPLE 19

Preparation of Terephthaloyl Isocyanate 32.38 g (0.2 mol) of terephthalamide and 200 g of 1,2-dichloroethane are introduced into a 500 ml reactor. 16.7 g (0.47 mol) of gaseous hydrochloric acid are then bubbled into the stirred suspension-solution of terephthalamide for 40 minutes. During addition, the temperature of the medium rises from 20° C. to 25° C. A white, solid suspension of terephthalamide hydrochloride is thus produced. It is characterized by its $^1$H NMR spectrum (CDCl$_3$, ppm): 3.37 (H of NH).

101.6 g (0.8 mol) of oxalyl chloride are then added drop by drop to the stirred terephthalamide hydrochloride suspension at 22° C., for 30 minutes, without cooling. The medium is stirred for a further 30 minutes at 25° C., and it is then heated at 68° C. for 135 minutes.

The remaining solids are then removed by filtration under reduced pressure. The IR spectrum of the terephthaloyl isocyanate obtained shows an absorption at 2230 cm$^{-1}$. The yield calculated from the urea produced by reaction of the terephtaloyl isocyanate with aniline is 78%.

EXAMPLE 20

Preparation of Adipoyl Isocyanate 8.64 g (0.06 mol) of adipamide and 100 g of 1,2-dichloroethane are introduced into a 300 ml reactor. 11.9 g (0.32 mol) of gaseous HCl are then bubbled into the stirred suspension-solution of adipamide for 50 minutes. During this addition, the temperature of the medium rises from 28° C. to 31° C. A white, solid suspension of adipamide hydrochloride is thus produced. It is characterized by its $^1$H NMR spectrum (DMSO, ppm): 1.45; 2.03 (H, methylenic), 5.51 (H of NH).

68.5 g (0.54 mol) of oxalyl chloride are then added drop by drop to the stirred adipamide hydrochloride suspension-solution for 20 minutes, without cooling. The temperature of the medium decreases from 33° C. to 30° C. The medium is stirred for a further 30 minutes at 30° C. It is then heated at 80° C. for 1.5 hours. The IR spectrum shows the adipoyl isocyanate absorption at 2250 cm$^{-1}$ (NCO).

EXAMPLE 21

Preparation of Adipoyl Isocyanate (Comparative Example)

This example is not part of the invention.

8.64 g (0.06 mol) of adipamide and 100 g of 1,2-dichloroethane are introduced into a 300 ml reactor. 68.5 g (0.54 mol) of oxalyl chloride are then added to the stirred suspension-solution of adipamide. In order to avoid a considerable heat release in the reaction medium, this addition is made drop by drop for 180 minutes. The temperature of the medium rises from 28° C. to 31° C. The medium is stirred for a further 30 minutes at 31° C. It is then heated at 80° C. The IR spectrum shows the adipoyl isocyanate absorption at 2250 cm$^{-1}$ (NCO) only after 12 hours of heating.

EXAMPLE 22

Preparation of Fumaroyl Isocyanate 10.27 g (0.09 mol) of fumaramide and 400 g of 1,2-dichloroethane are introduced into a 500 ml reactor. 10.44 g (0.28 mol) of gaseous HCl are then bubbled into the suspension-solution of fumaramide for 25 minutes. During this addition, the temperature of the medium rises from 25° C. to 32° C. A white, solid suspension of fumaramide hydrochloride is thus produced. It is characterized by its $^1$H NMR spectrum (DMSO, ppm): 6.77 (H, methylenic).

111.8 g (0.90 mol) of oxalyl chloride are then added drop by drop to the stirred fumaramide hydrochloride suspension-solution for 20 minutes, without cooling. The temperature remains at 24° C. The medium is stirred for a further 60 minutes at 24° C. It is then heated at 83° C. for 3.5 hours.

The remaining solids are then removed by filtration under reduced pressure. The IR spectrum of the fumaroyl isocyanate obtained shows an absorption at 2240 cm$^{-1}$. The yield calculated from the quantity of the urea obtained by reaction of the fumaroyl isocyanate with aniline is 61.5 %.

EXAMPLE 23

Preparation of Tert-butyloxycarbonyl Isocyanate 4.0 g (0.034 mol) of tert-butylcarbamate and 80 g of 1,2-dichlorethane are introduced into a 100 ml reactor. As the tert-butylcarbamate is unstable at room temperature when hydrochloric acid is present, the suspension-solution of t-butylcarbamate is cooled at 0° C. and 1.9 g (0.051 mol) of gaseous hydrochloric acid are then bubbled into this stirred suspension-solution for 90 minutes. During this addition, the temperature of the medium rises from 0° C. to 3° C. A white, solid suspension of t-butylcarbamate hydrochloride is thus produced.

8.3g (0.063 mol) of oxalyl chloride are then added drop by drop to the stirred suspension-solution of t-butylcarbamate hydrochloride at 0° C. for 20 minutes. The temperature of the medium rises from 0° to 2° C. The medium is stirred at 0° C. for a further 90 minutes. It is then heated at 80° C. for 11 hours.

The remaining solids are then removed by filtration under reduced pressure. The IR spectum of the t-butyloxycarbonyl isocyanate obtained shows an absorption at 2250 cm$^{-1}$. The yield calculated from the urea produced by reaction of the t-butyloxycarbonyl isocyanate with aniline is 47.8%.

EXAMPLE 24

Preparation of n-butyryl Isocyanate 25.8 g (0.30 mol) of n-butyramide and 200 g of 1,2-dichloroethane are introduced into a 500 ml reactor. 13.6 g (0.36 mol) of gaseous HCl are then bubbled into the suspension-solution of n-butyramide for 40 minutes. During this addition, the temperature of the medium rises from 20° C. to 23° C. A white, solid suspension of butyramide hydrochloride is thus produced. It is characterized by its $^1$H NMR spectrum.

42.0 g (0.33 mol) of oxalyl chloride are then added drop by drop to the stirred butyramide hydrochloride suspension-solution for 60 minutes, without cooling. The temperature of the medium decreases from 23° C. to 20° C. The medium is stirred for a further 60 minutes at 20° C. It is then heated at 120° C. for 3 hours.

The remaining solids are then removed by filtration under reduced pressure. The n-butyryl isocyanate is then isolated by distillation under reduced pressure.

bp: 64° C./40 mm Hg

Yield: 86%

We claim:

1. A process for preparing an acyl isocyanate comprising (a) reacting oxalyl chloride with a salt selected from the group consisting of a carboxamide hydrohalide, a carbamate hydrohalide, a carboxamide sulphate, a carbamate sulphate and a mixture thereof, wherein the nitrogen atom of said carboxamide and said carbamate is unsubstituted and (b) heating the resulting reaction mixture at a temperature ranging from 30° C. to 150° C.

2. The process of claim 1 wherein said salt is a carboxamide hydrochloride, a carbamate hydrochloride or a mixture thereof.

3. The process of claim 1 carried out in an inert aprotic solvent medium.

4. The process of claim 3 wherein said inert aprotic solvent medium is selected from the group consisting of an aliphatic hydrocarbon, an aliphatic halogenated hydrocarbon, a cycloalkane, an aromatic hydrocarbon and a mixture thereof.

5. The process of claim 1 wherein said oxalyl chloride is reacted with said salt without cooling said reaction mixture.

6. The process of claim 1 wherein 1 to 1.2 equivalents of oxalyl chloride are used for each amide salt function or carbamate salt function to be reacted.

7. The process of claim 1 which includes introducing said salt into a solvent medium and thereafter adding said oxalyl chloride to said salt containing solvent medium.

8. The process of claim 1 wherein said salt has the formula $Z(CONH_2)_n \cdot y(H_mX)$ wherein Z represents a mono- or divalent radical selected from the group consisting of
(a) a linear or branched, saturated or unsaturated, substituted or unsubstituted aliphatic radical having 1 to 20 carbon atoms,
(b) a saturated or unsaturated, substituted or unsubstituted cycloaliphatic radical having 5 to 7 carbon atoms,
(c) a linear or branched, saturated or unsaturated, substituted or unsubstituted araliphatic radical having 7 to 20 carbon atoms,
(d) a substituted or unsubstituted phenyl, phenylene, naphthyl or naphthalene radical,
(e) a saturated or unsaturated, substituted or unsubstituted 5- or 6-membered heterocyclic radical having at least one hetero atom selected from the group consisting of oxygen and nitrogen or Z represents RO—, —OR—O— or —R—O— wherein R represents a mono- or divalent radical selected from the group consisting of
(a') a linear or branched, saturated or unsaturated, substituted or unsubstituted aliphatic radical having 1 to 8 carbon atoms,
(b') a saturated or unsaturated, substituted or unsubstituted cycloaliphatic radical having 5 to 7 carbon atoms,
(c') a linear or branched, saturated or unsaturated, substituted or unsubstituted araliphatic radical having 7 to 11 carbon atoms, and
(d') a substituted or unsubstituted phenyl, phenylene, naphthyl or naphthalene radical, n represents 1 or 2,
m represents 1 or 2,
y represents n/m, and
X represents halogen, $SO_4$ or $HSO_4$.

9. The process of claim 8 wherein Z is substituted by a substituent selected from the group consisting of halogen, a hydrocarbyloxy radical having 1 to 20 carbon atoms and a halohydrocarbyloxy radical having 1 to 20 carbon atoms and when Z contains an aromatic or heteroaromatic cycle said substituent is further selected from the group consisting of a hydrocarbyl radical having from 1 to 20 carbon atoms, a halohydrocarbyl radical having 1 to 20 carbon atoms and a nitro group.

10. The process of claim 8 wherein X represents halogen.

11. The process of claim 8 wherein said Z, representing an unsaturated aliphatic radical, is isopropenyl and wherein said process is carried out in a solvent medium, said solvent medium being a mixture of o-dichlorobenzene and an alkane selected from the group consisting of n-hexane, n-heptane and cyclohexane.

12. The process of claim 1 which includes precipitating the product resulting from step (a) prior to heating the reaction mixture in step (b).

13. A process for preparing an acyl isocyanate comprising (a) reacting oxalyl chloride with a salt selected from the group consisting of a carboxyamide hydrohalide, a carbamate hydrohalide, a carboxamide sulphate, a carbamate sulphate and a mixture thereof, (b) separating from the reaction mixture resulting from step (a) the reaction product of said oxalyl chloride and said salt and (c) heating said reaction product at a temperature ranging from 30° C. to 150° C. optionally in the presence of a solvent medium.

* * * * *